United States Patent [19]

Graf et al.

[11] Patent Number: 4,648,992

[45] Date of Patent: Mar. 10, 1987

[54] WATER-SOLUBLE PHTHALOCYANINE COMPOUNDS

[75] Inventors: Gregor Graf, Basel; Gerd Hölzle, Liestal; Gerhard Reinert, Allschwil, all of Switzerland

[73] Assignee: Ciba-Geigy Corporation, Ardsley, N.Y.

[21] Appl. No.: 700,203

[22] Filed: Feb. 11, 1985

[30] Foreign Application Priority Data

Feb. 17, 1984 [CH] Switzerland .................... 779/84

[51] Int. Cl.$^4$ .......................................... C07D 487/22
[52] U.S. Cl. ........................................ 540/124; 8/111;
422/24; 540/123; 540/125; 540/127; 540/128;
540/130; 540/131; 540/132; 540/133; 540/134;
540/135; 540/140
[58] Field of Search .................... 252/94, 95, 102, 103,
252/524; 260/314, 242.2, 245.1, 245.73, 245.74,
245.76, 245.77, 245.78, 245.79, 245.8, 245.81,
245.86; 8/103, 107, 108, 110, 111

[56] References Cited

U.S. PATENT DOCUMENTS

| | | | |
|---|---|---|---|
| 3,094,534 | 6/1963 | Griot et al. | 260/313 |
| 3,094,535 | 6/1963 | Kenney et al. | 260/245.74 |
| 3,094,536 | 6/1963 | Kenney et al. | 260/245.74 |
| 3,927,967 | 12/1975 | Speakman | 8/103 |
| 4,033,718 | 7/1977 | Holcombe et al. | 8/103 |
| 4,077,768 | 3/1978 | Johnston et al. | 8/107 |
| 4,094,806 | 6/1978 | Wiers | 252/102 |
| 4,166,718 | 9/1979 | Reinert et al. | 8/111 |
| 4,318,883 | 3/1982 | Polony et al. | 422/22 |
| 4,456,452 | 6/1984 | Hölzle et al. | 8/103 |
| 4,497,741 | 2/1985 | Hölzle et al. | 260/245.77 |

FOREIGN PATENT DOCUMENTS

| | | |
|---|---|---|
| 0003149 | 7/1979 | European Pat. Off. |
| 0003371 | 8/1979 | European Pat. Off. |
| 0003861 | 9/1979 | European Pat. Off. |
| 0026744 | 4/1981 | European Pat. Off. |
| 0035470 | 9/1981 | European Pat. Off. |
| 0054992 | 6/1982 | European Pat. Off. |
| 0081462 | 1/1984 | European Pat. Off. |
| 1372035 | 10/1974 | United Kingdom |
| 1408144 | 10/1975 | United Kingdom |

OTHER PUBLICATIONS

Moser et al, Phthalocyanine Compounds, Reinhold Publishing Corp., New York, (1963), pp. 104 and 105.

*Primary Examiner*—Richard L. Raymond
*Attorney, Agent, or Firm*—Edward McC. Roberts; Kevin T. Mansfield

[57] ABSTRACT

Novel phthalocyanine compounds are described, which have the formula

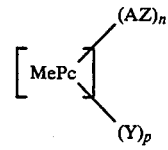

in which MePc is the Si(IV)-, P(V)-, Ti(IV)-, Ge(IV)-, Cr(IV)-, Ga(III)-, Zr(IV)-, In(III)-, Sn(IV)- or Hf(IV)-phthalocyanine or -naphthalocyanine ring system, A is an anionic, nonionic or cationic group which imparts solubility in water, Z is the counter-ion to A, if the latter is an ionic group, and is 0 if A is a nonionic group, n is any desired number from 1 to 8, Y is a neutral substituent which does not impart solubility in water and p is any desired number from 0 to 6, it being possible for the groups AZ and Y present in the molecule to be identical or different in either case, and the sum of n+p being not more than 8 and MePc not being the Sn(IV)-phthalocyanine or Sn(IV)-naphthalocyanine ring system if p is 0 and if the only groups imparting water-solubility in the molecule are sulfo groups. The novel compounds can be used as photoactivators, particularly for bleaching textiles and for controlling microorganisms in or on organic or inorganic substrates. Bleaching, washing and steeping agents and agents having antimicrobial activity, which contain the novel phthalocyanine compounds, are also described.

7 Claims, No Drawings

WATER-SOLUBLE PHTHALOCYANINE COMPOUNDS

The present invention relates to novel, water-soluble phthalocyanine compounds, processes for their preparation, their use as photoactivators (photosensitisers) or singlet oxygen producers, in particular for bleaching or removing spots from textiles and for controlling microorganisms in or on organic or inorganic substrates, and to bleaching agents, washing agents, rinsing agents and steeping agents and antimicrobial agents containing the novel phthalocyanine compounds.

It is known that various water-soluble phthalocyanine compounds, in particular those having zinc and aluminium as the central atom, have a photosensitising action and can therefore be used as photobleaching agents or antimicrobial active compounds. In this context, see, inter alia, U.S. Pat. Nos. 3,927,967, 4,033,718, 4,166,718 and 4,094,806; DE A-2,222,829, 2,627,449 and 2,812,261; and EP A-3,149, 3,371, 3,861, 26,744, 35,470, 47,716, 54,992 and 81,462. The publications mentioned also describe agents containing the said water-soluble phthalocyanine compounds.

The novel, water-soluble phthalocyanine compounds according to the present invention contain Si(IV), P(V), Ge(IV), Ti(IV), Cr(VI), Ga(III), Zr(IV), In(III), Sn(IV) or Hf(IV) as the central atom. They have the general formula

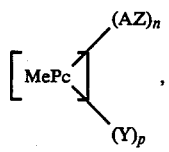     (1)

in which MePc is the Si(IV)-, P(V)-, Ti(IV)-, Ge(IV)-, Cr(VI)-, Ga(III)-, Zr(IV)-, In(III)-, Sn(IV)- or Hf(IV)-phthalocyanine or -naphthalocyanine ring system, A is an anionic, nonionic or cationic group which imparts solubility in water, Z is the counter-ion to A, if the latter is an ionic group, and is 0 if A is a nonionic group, n is any desired number from 1 to 8, Y is a neutral substituent which does not impart solubility in water and p is any desired number from 0 to 6, it being possible for the groups AZ and Y present in the molecule to be identical or different in either case, and the sum of n + p being not more than 8 and MePc not being the Sn(IV)-phthalocyanine or Sn(IV)-naphthalocyanine ring system if p is 0 and if the only groups imparting water-solubility in the molecule are sulfo groups.

As is adequately known from phthalocyanine chemistry, the free valences of the central atoms are saturated, depending on their valency, by one or more additional ligands, for example anions. These anions can, for example, be identical with the anions of the particular compound used for the preparation of the complex. Examples of anions of this type are halide, sulfate, nitrate, phosphate or hydroxyl ions or ions of organic carboxylic acids (for example the acetate or formate ion) or of sulfonic acids (for example the tosylate ion). Some central atoms of fairly high valency can also be in the form of oxo ions, for example $ZrO^{2+}$, $TiO^{2+}$, $CrO_2^{2+}$ and the like.

It is also known from phthalocyanine chemistry that the phthalocyanine compounds are frequently not single substances, but are often mixtures. The number of substituents (degree of substitution) present in the molecule is therefore seldom an integer (n or p not integral). It is also to be noted that the individual substituents A or Y can be identical or different in each case, i.e. entirely different substituents imparting solubility in water or neutral substituents, respectively, can also be present in a molecule. The substituents imparting solubility in water can either be of the same type (cationic, anionic or nonionic) or they can belong to different types, in which case any combination (anionic/nonionic, cationic/nonionic, anionic/cationic and anionic/nonionic/cationic) is possible. All the substituents A and Y are attached to the phenyl ring of the phthalocyanine or naphthalocyanine ring system.

"Naphthalocyanine ring system" is to be understood as meaning a phthalocyanine ring system in which a further benzene nucleus is fused to each of the 4 benzene radicals, attachment in the 2,3-position or the 1,2-position being possible, corresponding to the two partial structures

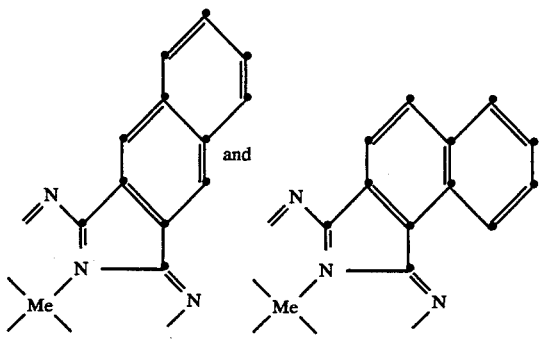

Z is any desired counter-ion to an ionic group A. If a group A contains several ionic radicals, Z can have the same valency as the group A or a corresponding number of monovalent counter-ions Z can be present. If A is nonionic, Z is zero. The following are examples of cationic counter-ions: the hydrogen ion, alkali metal and alkaline earth metal ions and unsubstituted and substituted ammonium ions. Substituted ammonium ions are derived, for example, from primary, secondary or tertiary aliphatic or cyclic amines. Examples of these ions are ammonium ions of the formula

in which R', R" and R''' independently of one another are hydrogen or alkyl (preferably having 1-4 C atoms) which is unsubstituted or substituted by halogen, hydroxyl, phenyl or cyano, at least one R-substituent being other than hydrogen. Two R-radicals together can also form the groups needed to complete a saturated 5-membered or 6-membered nitrogen heterocyclic structure, and this can, if desired, also contain, additionally, an oxygen or nitrogen atom as a member of the ring. The following are examples of heterocyclic structures of this type: piperidine, piperazine, morpholine, pyrrolidine, imidazolidine and the like.

Preferred cationic counter-ions are the hydrogen ion, alkali metal ions (particularly Na+ and K+) and ammonium ions.

Suitable counter-ions for cationic groups A are any desired anion, and these are introduced, as a rule, by the process of preparation (quaternisation). The following are examples of anions of this type: halogen ions (including $I^{\ominus}$), alkylsulfate ions or arylsulfonate ions, such as the benzenesulfonate, naphthalenesulfonate, p-tolylsulfonate and p-chlorophenylsulfonate ion; also sulfate, methylsulfate, sulfite, aminosulfonate, bicarbonate, carbonate, perchlorate, phosphate, nitrate, acetate, propionate, oxalate, maleate, citrate, lactate, succinate, chloroacetate, tartrate, malate, methanesulfonate or benzoate ions or another anion of an organic carboxylic acid. The anions can be readily exchanged with one another by customary methods.

As mentioned above, anionic groups are examples of groups A which impart solubility in water. Any anionic groups or radicals containing such groups which impart an adequate solubility in water to the phthalocyanine compounds are suitable in this respect, particularly those which are already known from phthalocyanine chemistry.

Examples of such anionic groups which impart solubility in water are sulfo, carboxyl, phosphate, sulfate, sulfinyl, disulfimide and cyanimide groups or radicals containing one or more of the abovementioned groups.

A can, for example, be one or more of the following groups:

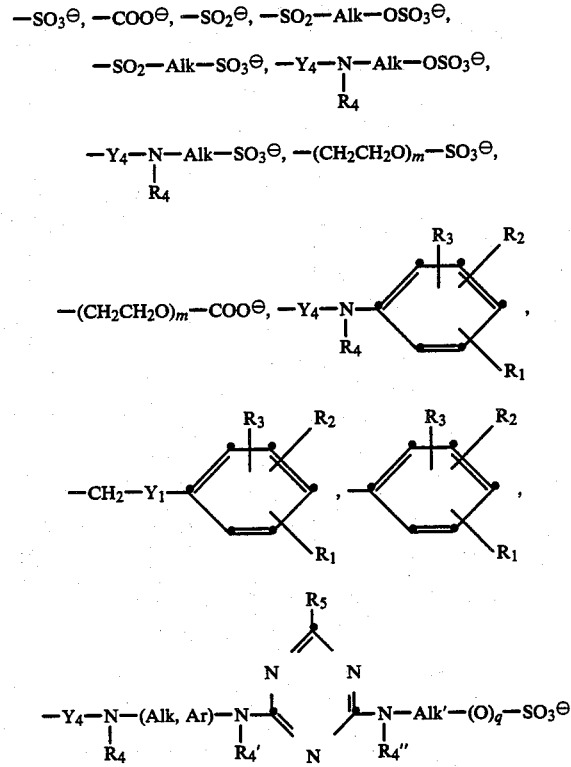

$-SO_2N^{\ominus}-CN$ or $-SO_2N^{\ominus}-SO_2R_6$ in which $R_1$, $R_2$ and $r_3$ independently of one another are hydrogen, alkyl, hydroxyl, $SO_3^{\ominus}$ or $-COO^{\ominus}$, at least one of these substituents being $SO_3^{\ominus}$ or $COO^{\ominus}$, $R_4$, $R'_4$ and $R''_4$ independently of one another are substituted or unsubstituted alkyl or hydrogen, $R_5$ is hydrogen or halogen, $R_6$ is substituted or unsubstituted alkyl or substituted or unsubstituted phenyl or naphthyl, Ar is a substituted or unsubstituted phenyl or naphthyl radical, Alk and Alk' are each a substituted or unsubstituted alkylene group, $Y_1$ is $-N-R_4$ or S, $Y_4$ is $-SO_2-$ or $-CO-$, preferably $-SO_2-$, m is a number from 1 to 30 and q is 0 or 1. $Y_4$ is preferably $-SO_2-$; of the radicals $R_1$, $R_2$ and $R_3$, $R_1$ is preferably $SO_3^{\ominus}$, $R_2$ is preferably hydrogen, $SO_3^{\ominus}$, alkyl or hydroxy, especially hydrogen, and $R_3$ is preferably hydrogen.

If phenyl or naphthyl rings are substituted, they contain, for example, 1 to 3 substituents, preferably one substituent. The following are examples of such substituents: alkyl or alkoxy, nitro, halogenoalkyl, halogen, alkoxycarbonyl, cyano, alkylsulfonyl, acylamino, carboxyl and derivatives thereof, sulfo and derivatives thereof, acyloxy, trifluoromethyl and dialkylamino.

Halogen is, in particular, fluorine, chlorine or bromine, preferably chlorine. Examples which should be mentioned of derivatives of the carboxyl and sulfo groups are their salts, esters and amides.

If alkylene or alkyl groups are substituted (for example radicals $R_4$, $R_6$ and Alk), the following are examples of suitable substituents: hydroxyl, alkoxy, halogen, cyano, aryl (in particular phenyl or naphthyl which can be substituted like the aromatic groups $R_6$), carboalkoxy, aminocarbonyl or dialkylamino.

Alkyl, alkylene and alkoxy groups as such or in composite groups containing alkyl or alkoxy groups, have, for example, 1 to 8, especially 1 to 6 and preferably 1 to 4, C atoms. Alkyl radicals in carboxylic acid ester or carboxamide groups or in sulfonamide groups preferably have 1 to 8 C atoms. These preferred chain lengths apply to all the alkyl, alkylene and alkoxy groups in the present description, unless otherwise specified.

$Y_1$ is preferably $N-R_4$ in the above formulae. $R_4$ is preferably hydrogen or unsubstituted alkyl, especially hydrogen. Alkylene groups (Alk or Alk') are preferably unsubstituted.

The following are preferred anionic groups A: $-SO_3^{\ominus}$, $-COO^{\ominus}$, $-SO_2^{\ominus}$, $-SO_2N^{\ominus}-CN$ or $-SO_2N^{\ominus}-SO_2-R'_6$ in which $R'_6$ is $C_1-C_4$-alkyl, phenyl, $(C_1-C_4$-alkyl)-phenyl, chlorophenyl or methoxyphenyl, in particular the group $SO_3^{\ominus}$. Suitable cations Z are then a hydrogen ion, an alkali metal ion or an unsubstituted or substituted ammonium ion, especially a hydrogen, sodium or ammonium ion.

Cationic groups are also suitable as groups A which impart solubility in water. Any cationic group or radical containing such groups which imparts an adequate solubility in water to the phthalocyanine compounds is suitable, in particular groups which are already known from phthalocyanine chemistry.

Examples of such cationic groups which impart solubility in water are quaternary ammonium compounds or tertiary sulfonium groups or radicals containing one or more of the abovementioned groups. The quaternary ammonium compounds can be derived from aliphatic amines or from nitrogen-containing aromatic or non-aromatic heterocyclic compounds.

Thus A can, for example, represent one or more groups of the following formulae:

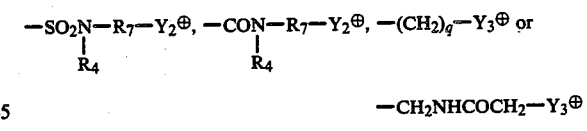

$-CH_2NHCOCH_2-Y_3^{\oplus}$ in which q is 0 or 1, $R_7$ is unbranched or branched alkylene having 1 to 8 C atoms or 1,3-phenylene or 1,4-phenylene, $R_4$ is hydrogen or substituted or unsubstituted alkyl, $Y_2^{\oplus}$ is a group of the formula

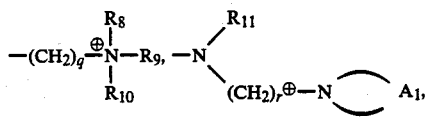

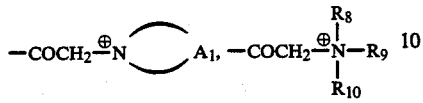

or in the event that $R_7$=alkylene, $Y_2^{\oplus}$ is also a group of the formula

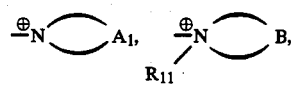

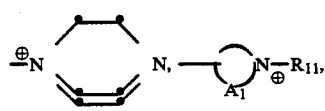

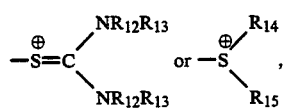

and $Y_3^{\oplus}$ is a group of the formula

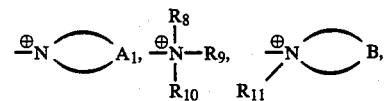

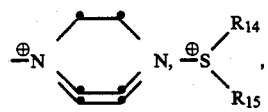

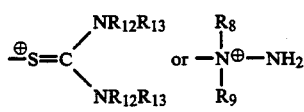

q in the above formulae being 0 or 1, $R_8$ and $R_9$ independently of one another being substituted or unsubstituted alkyl having 1 to 6 C atoms, $R_{10}$ being substituted or unsubstituted alkyl having 1 to 6 C atoms, cycloalkyl having 3 to 7 C atoms or the group $NR_{12}R_{13}$, $R_{11}$ being alkyl, $R_{12}$ and $R_{13}$ independently of one another being hydrogen or substituted or unsubstituted alkyl, $R_{14}$ and $R_{15}$ independently of one another being a substituted or unsubstituted alkyl or aralkyl radical, r being an integer from 1 to 6, $A_1$ being the groups needed to complete an aromatic, 5-membered to 7-membered nitrogen heterocyclic structure which can, if desired, also contain 1 or 2 further nitrogen atoms as ring members and which can, if desired, carry different substituents, and B being the groups needed to complete a saturated, 5-membered to 7-membered nitrogen heterocyclic structure which can, if desired, also contain 1 to 2 nitrogen, oxygen and/or sulfur atoms as ring members and which can, if desired, carry different further substituents.

Examples of substituents which can be present in optionally substituted alkyl groups are halogen, hydroxyl, cyano, phenyl, carboxyl, carboalkoxy or alkoxy. Suitable substituted alkyl groups are benzyl, phenethyl, hydroxyalkyl and cyanoalkyl. Cycloalkyl groups preferably have 5 or 6 C atoms; cyclohexyl is preferred.

Suitable aralkyl radicals are, in particular, alkyl radicals substituted by phenyl, naphthyl or pyridyl. The benzyl radical is preferred.

Suitable groups

are, in particular, the following:

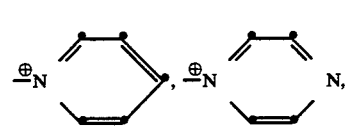

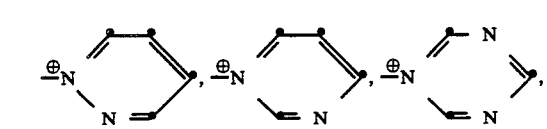

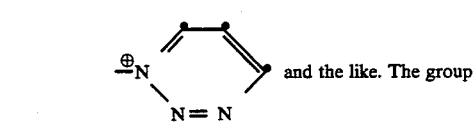

and the like. The group $N = N$

 is preferred.

Suitable heterocyclic rings in the group

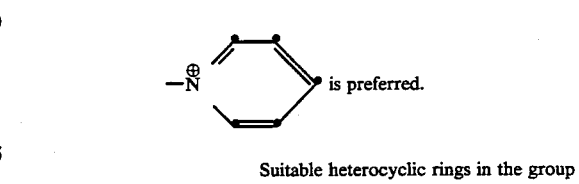

are also those which have just been mentioned, only the linkage to the residual substituents being effected via a carbon atom.

In all the substituents, phenyl, naphthyl and aromatic heterocyclic rings can be substituted by one or two further radicals, for example by alkyl, alkoxy, halogen, carboxyl, carboalkoxy, hydroxyl, amino, cyano, sulfo, sulfonamido, and the like. A substituent from the group comprising alkyl, alkoxy, halogen, carboxyl, carboalkoxy or hydroxyl is preferred.

The following are particularly suitable as the group

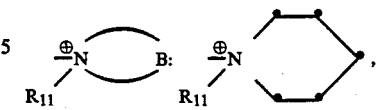

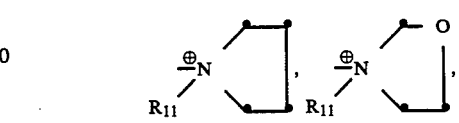

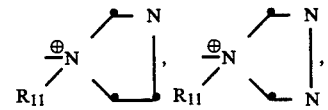

-continued

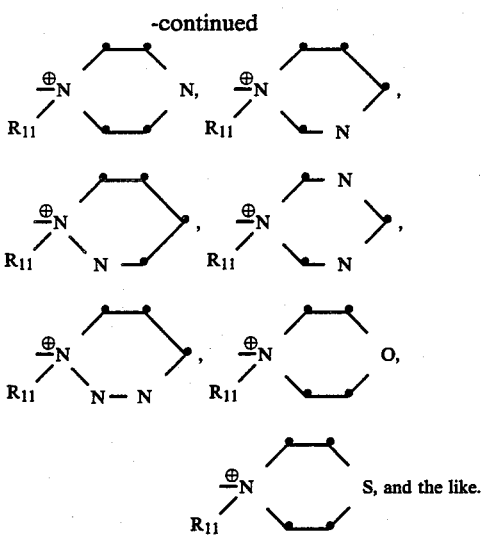

All the saturated nitrogen heterocyclic structures mentioned above can also be substituted by alkyl groups, either at a carbon atom or at a further nitrogen atom located in the ring. In this connection, the preferred alkyl group is the methyl group.

Groups which are preferred in this connection are those of the formula

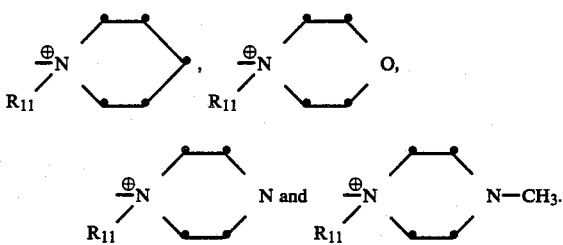

The possible meanings of Z in the event that A is a cationic group have already been listed earlier in the text. The following are preferred anions Z: halogen ions (including $I^{\ominus}$), alkylsulfate ions and arylsulfonate ions, for example a benzene sulfonate, naphthalenesulfonate, p-tolylsulfonate or p-chlorophenylsulfonate ion.

In the above definitions of substituents, halogen is chlorine, bromine, fluorine and iodine, especially chlorine or bromine and preferably chlorine. $R_4$ has the same preferred meaning as in the case of the anionic groups A.

As a cationic group, A is preferably a group of the formula $-SO_2NHR_7'-Y_2'^{\oplus}$ in which $R_7'$ is alkylene having 2 to 6 C atoms and $Y_2'^{\oplus}$ is a group of the formula

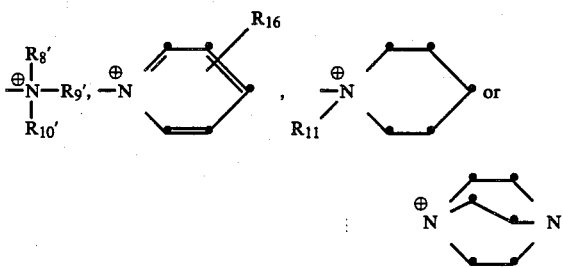

in which $R_8'$ and $R_9'^{\oplus}$ independently of one another are alkyl which has 1 to 4 C atoms and is unsubstituted or substituted by hydroxyl, cyano, halogen or phenyl, $R_{10}$ has the possible meanings of $R_8$ and can additionally be cyclohexyl or the amino group and $R_{11}$ is $C_1$-$C_4$-alkyl and $R_{16}$ is $C_1$-$C_4$-alkyl, $C_1$-$C_4$-alkoxy, halogen, carboxyl, carboalkoxy or hydroxyl.

The third type of substituents A constitutes the nonionic groups which impart solubility in water. Here too, any group of this type which imparts an adequate solubility in water to the phthalocyanine compounds is suitable. These are, again, especially groups which are known for this purpose from phthalocyanine chemistry. In the case of these groups, Z is zero.

Examples of nonionic groups A are those of the formulae

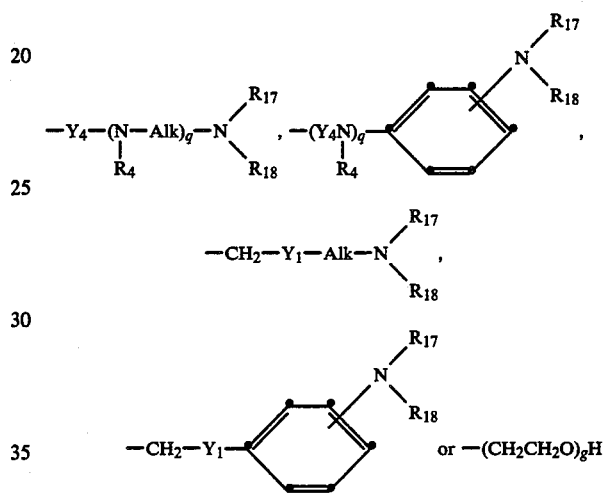

in which $Y_1$ is S or $NR_4$, $Y_4$ is $-SO_2-$ or $-CO-$, preferably $-SO_2-$, Alk is substituted or unsubstituted alkylene, $R_{17}$ and $R_{18}$ independently of one another are hydrogen, alkyl, hydroxyalkyl, cyanoalkyl, sulfoalkyl, carboxyalkyl or halogenoalkyl, phenyl which is unsubstituted or substituted by halogen, alkyl or alkoxy, sulfo or carboxyl, or $R_{17}$ and $R_{18}$, together with the nitrogen atom to which they are attached, are a saturated, 5-membered or 6-membered heterocyclic ring which can, in addition, also contain a nitrogen or oxygen atom as a member of the ring, $R_4$ is hydrogen or substituted or unsubstituted alkyl, q is 0 or 1 and g is a number from 4 to 50.

If alkylene (the radical Alk) or alkyl (the radical $R_4$) are substituted, examples of suitable substituents are hydroxyl, alkoxy, halogen, cyano, aryl (in particular phenyl or naphthyl which can be substituted, like the aromatic groups $R_6$), carboalkoxy, aminocarbonyl or dialkylamino. Preferably, however, the radical Alk or $R_4$ is unsubstituted. $Y_4$ is preferably $-SO_2-$; $R_4$ is preferably hydrogen. Preferred heterocyclic rings which can be formed by $R_{17}$ and $R_{18}$ conjointly with the nitrogen atom, are the morpholine, piperidine, pyrazoline, piperazine and oxazolidine radical. $R_{17}$ and $R_{18}$ preferably only form a heterocyclic ring if the group $-NR_{17}R_{18}$ is attached to an alkylene radical. The index g is preferably a number from 8 to 40, especially 10 to 30.

Preferred nonionic groups A are those of the formula

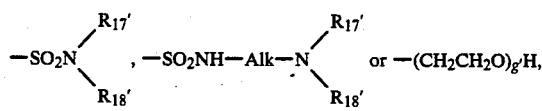

in which Alk is $C_2$-$C_6$-alkylene, $R'_{17}$ and $R'_{18}$ independently of one another are hydrogen, alkyl, hydroxyalkyl, cyanoalkyl or halogenoalkyl having 1 to 6 C atoms, or phenyl or, together with the nitrogen atom to which they are attached, are the piperidine, piperazine or morpholine ring, and g' is a number from 8 to 40.

The following should be mentioned as neutral substituents Y which do not impart solubility in water: halogen (for example fluorine, chlorine, bromine or iodine, especially chlorine or bromine and preferably chlorine), cyano, nitro, substituted or unsubstituted alkyl or substituted or unsubstituted phenyl. Alkyl groups preferably have 1-6, especially 1-4, C atoms. If such alkyl groups are substituted, examples of suitable substituents are hydroxyl, alkoxy, halogen, cyano, substituted or unsubstituted phenyl, carboalkoxy or aminocarbonyl. Examples of possible substituents of phenyl groups (including phenylalkyl) are alkyl, alkoxy, nitro, halogenoalkyl, halogen, alkoxycarbonyl, cyano, alkylsulfonyl, acylamino, acyloxy or trifluoromethyl.

Preferred substituents Y are halogen (especially chlorine and bromine), alkyl, phenyl, halogenophenyl, alkylphenyl and alkoxyphenyl, especially chlorine, bromine, $C_1$-$C_4$-alkyl or phenyl.

In formula (1), n is preferably any desired number from 1 to 4 and p is any desired number from 0 to 4. The number of substituents imparting solubility in water which must be present as a minimum in the molecule also depends on the number of substituents Y present. Regardless of whether groups imparting solubility in water are present or not (p=0), in every case sufficient groups imparting solubility in water must be present in the molecule to ensure an adequate solubility in water. A minimum solubility of only 0.001 g/l can be sufficient; in general a minimum solubility of 0.1 to 20 g/l is advantageous.

The indices n and p (provided that p is not in any case zero) can be any desired numbers within the range indicated. As is customary in phthalocyanine chemistry, the individual products frequently consist of mixtures, since products which are not single substances are often formed in the course of preparation (for example sulfonation, sulfochlorination, halogenation and the like). The indices therefore represent the "degree of substitution", which does not, of course, have to be integral.

As already mentioned earlier in the text, phthalocyanines according to the invention contain, for example, only one type of group which imparts solubility in water (anionic, cationic or nonionic). They can, however, also contain 2 or 3 types of these groups in the molecule, i.e. anionic and cationic, cationic and nonionic, anionic and nonionic and also anionic, nonionic and cationic. Examples are given below of two formulae of such phthalocyanines containing mixed substituents:

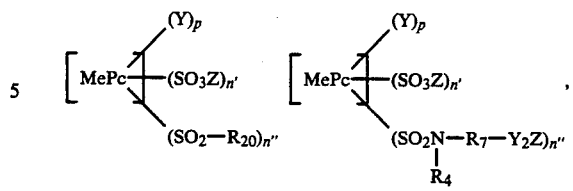

in which $n'+n''=n$ and $R_{20}=Z$ or $-NZCN$ or $NZ-SO_2-R_6$ and all the other general symbols are as defined above.

In formula (1) and in the compounds, according to the invention, which are described above and are preferred in respect of substituents, MePc is, in particular, the Si(IV)-, P(V)-, Ti(IV)-, Cr(VI)-, Ga(III)-, Ge(IV)- or Zr(IV)-phthalocyanine or -naphthalocyanine ring system, preferably -phthalocyanine ring system, and is especially the Ti(IV)-, Ga(III)-, Ge(IV)- or Zr(IV)-phthalocyanine or -naphthalocyanine ring system, preferably -phthalocyanine ring system. MePc is particularly preferentially the Ge(IV)-phthalocyanine ring system.

Compounds which should be singled out particularly within the scope of the formula (1) are those in which A is a group of the formula

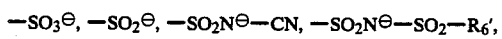

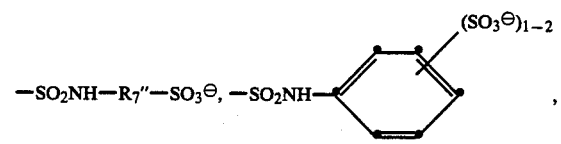

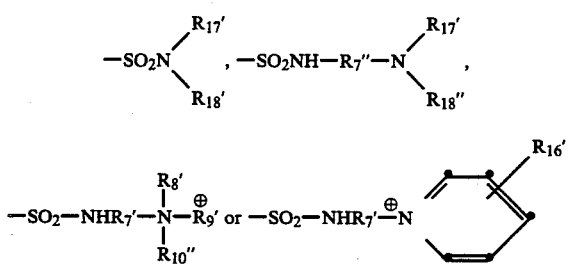

Z, as a counter-ion for anionic groups, is a hydrogen ion, alkali metal ion or unsubstituted or substituted ammonium ion, for cationic groups is a halide ion, alkylsulfate ion, a substituted or unsubstituted phenylsulfonate ion, a sulfate ion or a phosphate ion or the ion of an organic carboxylic acid, and, for nonionic groups, is 0, n is any desired number from 1 to 4, p is any desired number from 0 to 4 and Y is halogen, alkyl or phenyl, $R'_6$ in the above formulae being $C_1$-$C_4$-alkyl, phenyl, ($C_1$-$C_4$-alkyl)-phenyl, chlorophenyl or methoxyphenyl, $R'_7$ being $C_2$-$C_6$-alkylene, $R''_7$ being $C_1$-$C_6$-alkylene, $R'_8$, $R'_9$ and $R''_{10}$ independently of one another being $C_1$-$C_4$-alkyl which is unsubstituted or substituted by hydroxyl, halogen or phenyl, $R'_{16}$ is $C_1$-$C_4$-alkyl, halogen or hydroxyl and $R'_{17}$ and $R'_{18}$ independently of one another are hydrogen, alkyl, hydroxyalkyl or halogenoalkyl having 1-6 C atoms in each case, or phenyl or, together with the nitrogen atom to which they are attached, are the piperidine, piperazine or morpholine ring, it being possible for different types of substituents A and/or Y to be present in the molecule, in particular compounds in which A is a group of the formula —SO$_3^\ominus$, —SO$_2$N$^\ominus$—CN or SO$_2$N$^\ominus$—SO$_2$—R'$_6$ in which R'$_6$ is as defined above and Z is a hydrogen, alkali metal or ammonium ion.

Phthalocyanine compounds which are particularly preferred in this respect are those in which A is SO$_3^\ominus$, Z is a hydrogen, alkali metal or ammonium ion, n is any desired number from 1 to 4, preferably 2 to 4, and p is any desired number from 0 to 4, preferably from 0 to 2.

In the compounds, according to the invention, which are described above as especially to be singled out or especially preferred, MePc is, in particular, the Ti(IV)-, Ge(IV)- or Zr(IV)-phthalocyanine ring system, preferably the Ge(IV)-phthalocyanine ring system.

The compounds, according to the invention, of the formula (1) can be prepared by processes which are known per se and are customary in phthalocyanine chemistry. In this respect, it is possible essentially to employ three different methods:

(a) The central atom is introduced into a metal-free (i.e. containing no central atom) phthalocyanine or naphthalocyanine which contains the substituents AZ imparting solubility in water, by reacting the phthalocyanine or naphthalocyanine with a suitable compound (for example a salt) of the central atom.

(b) The substituents imparting solubility in water are introduced into the appropriate metal phthalocyanines or naphthalocyanines (phthalocyanines having a central atom; phthalocyanine pigments) by means of suitable reactions.

(c) The substituents imparting solubility in water are already present in the starting materials (for example phthalic anhydride, phthalodinitrile and the corresponding naphthalenedicarboxylic acid derivatives) required for the synthesis of the phthalo(or naphthalo)-cyanine ring system. The synthesis of the ring system and the incorporation of the central atom are then effected by customary processes, either simultaneously or successively.

Depending on their nature, the substituents which do not impart solubility in water can also already be present in the starting materials, or they can be introduced into the synthesised ring system subsequently, for example by halogenation, either before or after the incorporation of the central atom. In some processes for the preparation of the phthalocyanine ring system, such substituents (for example chlorine) are also introduced directly, for example by using chlorides as catalysts and as salts of the central atom to be incorporated.

If process (a) above is used, the appropriately substituted phthalocyanines or naphthalocyanines without a central atom can, for example, be reacted with a compound of the appropriate central atom, for example with a salt thereof or with an alcoholate, if the central atom is a metal which forms alcoholates. Examples of solvents suitable for this reaction are mixtures of water and organic solvents, for instance tertiary amines, or anhydrous solvents, for example pyridine and chlorobenzenes. Resulting metal complexes can, of course, also be converted into other metal complexes. Process variant (a) is, for example, also described in U.S. Pat. No. 4,318,883.

The methods of introducing substituents into the ring system (alternative (b) above) are very numerous and vary depending on the nature of the substitution. Only a few examples of such methods will be given below:

The introduction of sulfonic acid groups (A=SO$_3^\ominus$) can be effected, for example, by sulfonation, for example by means of oleum. Alternatively, appropriate non-sulfonated phthalocyanines can also be reacted with chlorosulfonic acid to give the corresponding phthalocyanine sulfochlorides and the latter can then be hydrolysed to the sulfonic acids. In both cases the free sulfonic acid groups can subsequently be converted into their salts. Methods of sulfonation of this type are described, for example, in U.S. patent Application Ser. No. 4,318,883 and in EP A-47,716.

Carboxyl groups can be introduced into the unsubstituted phthalocyanines by reacting the latter with phosgene and aluminium chloride and hydrolysing the resulting acid chloride, or by reaction with trichloroacetic acid. The acid chlorides can also be converted into other water-soluble carboxylic acid derivatives in a known manner. Phthalocyanines substituted by carboxyl groups can also be prepared by synthesis from trimellitic acid.

The compounds of the formula (1) which are substituted by sulfonamide or carboxamide groups of the type shown in the following formulae

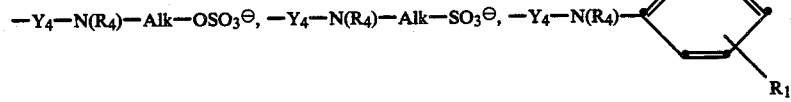

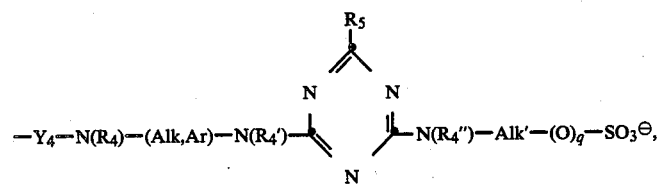

-continued

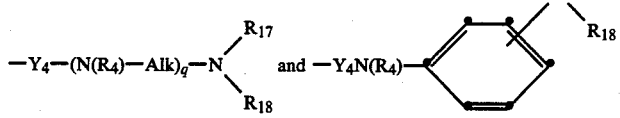
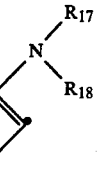

are obtained from the SO$_2$Cl-substituted or COCl-substituted, respectively, phthalocyanines described earlier in the text (obtained by reaction with chlorosulfonic acid or with phosgene and AlCl$_3$) by reaction with correspondingly substituted aliphatic or aromatic amines.

Compounds of the formula (1) which are substituted by groups of the formulae

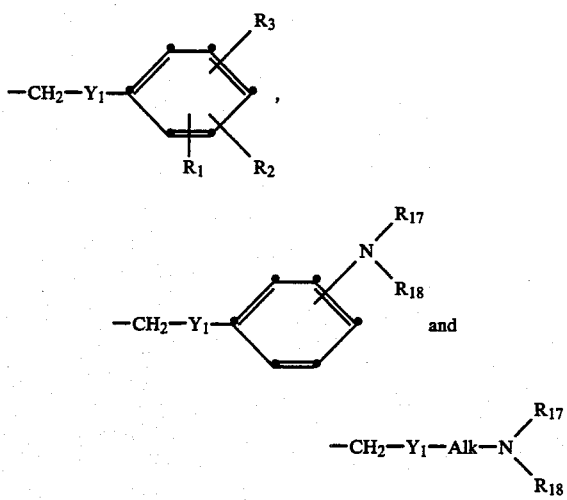

can be obtained by chloromethylating unsubstituted metal-free or metallised phthalocyanines, for example by reacting the latter with paraformaldehyde or bis-chloromethyl ether and anhydrous aluminium chloride in the presence of triethylamine, and by subsequently reacting the chloromethyl compounds with correspondingly substituted anilines or thiophenols or amines or mercaptans, respectively.

Compounds of the formula (1) which are substituted by groups of the formulae

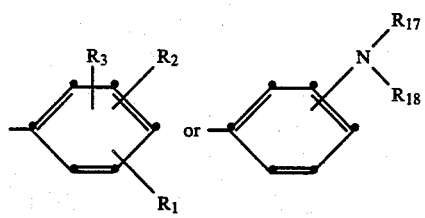

which impart solubility in water can be obtained, for example, if a correspondingly substituted phthalic anhydride or phthalodinitrile (or the corresponding naphthalenedicarboxylic acid derivatives) is used as the starting material and is reacted in a known manner to give the phthalocyanine ring system. If a substituted phthalodinitrile is used, this is fused, if desired together with a metal salt, or is cyclised to give the phthalocyanine ring system in solution or in suspension. If the corresponding phthalic anhydride is used, urea and, if desired, a catalyst, for example boric acid or ammonium molybdate are also added before the reaction. Other substituted phthalocyanines, for example the sulfonated phthalocyanines as well, can also be obtained in this manner.

The processes mentioned above are also described in U.S. Pat. No. 4,318,883.

Compounds of the formula (1) in which A is a group of the formula SO$_2$N$^\ominus$—CN, —SO$_2$N$^\ominus$—SO$_2$—R$_6$ or —SO$_2^\ominus$ are prepared, for example, by reacting the corresponding phthalocyanine (naphthalocyanine) with chlorosulfonic acid and by reacting the resulting sulfochloride further with cyanamide, or with ammonia and a halide of the formula Hal—SO$_2$—R$_6$ (Hal=halogen, in particular chlorine), or with hydrazine or a hydrazine derivative. The corresponding processes are described, for example, in EP A-81,462.

Compounds of the formula (1) containing —(CH$_2$CH$_2$O)$_m$— —SO$_3^\ominus$ or —(CH$_2$CH$_2$O)$_g$H groups are obtained, for example by using phthalocyanines or naphthalocyanines which are substituted by hydroxyl groups and have already been metallised or are still metal-free as the starting materials, and reacting them with ethylene oxide. The reaction product can then be esterified, for example with sulfuric acid. Compounds of the formula (1) containing sulfate, carboxylate, methoxycarboxylate, polyethoxycarboxylate, phosphate and polyethoxyphosphate groups can also be prepared from the said hydroxysubstituted phthalocyanines. Processes of this type are mentioned in EP A-3,149.

The introduction of cationic substituents into the phthalocyanine or naphthalocyanine ring system which can already contain a central atom or into which the latter is only incorporated after the introduction of the substituents (method (a) above) is also effected by methods which are customary in phthalocyanine chemistry.

Compounds of the formula (1) in which A is a group —SO$_2$N(R$_4$)—R$_7$—Y$_2^\oplus$ or —CON(R$_4$)—R$_7$—Y$_2^\oplus$ are prepared, for example, by reacting the particular phthalocyanine with chlorosulfonic acid to give the corresponding sulfochloride compounds or by reacting it with phosgene and AlCl$_3$ to give the corresponding carboxylic acid chloride compounds. These sulfochloride-phthalocyanines or carboxylic acid chloride-phthalocyanines are then reacted in a known manner with a diamine or mercapto-amine of the formula

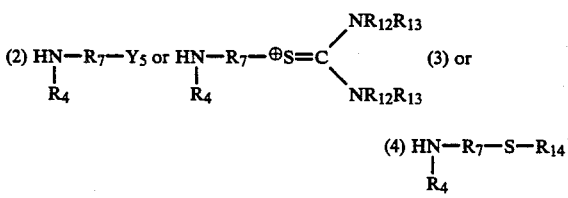

in which R$_7$, R$_{12}$ and R$_{13}$ are as defined above and Y$_5$ is a tertiary amino group which has not yet been quaternised. In the sulfonamido-phthalocyanines thus obtained, the tertiary amino group $Y_5$ is quaternised by known methods to give a group $Y_2^\oplus$ or the mercapto group in formula (4) is ternised to give the group

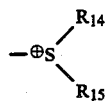

The phthalocyanine sulfochlorides or phthalocyaninecarboxylic acid chlorides can, however, also be reacted in a known manner with amines which already contain quaternary ammonium groups or ternary sulfonium groups, respectively (i.e. reaction with amines of the formula (2) in which $Y_5$ has been replaced by $Y_2^\oplus$ or the sulfur atom in the amine of the formula (4) has already been ternised).

A further method consists in reacting the phthalocyanine sulfochlorides or phthalocyaninecarboxylic acid halides with halogenoamines of the formula

(Hal=halogen) and, for example, reacting the resulting phthalocyanine sulfonamide or phthalocyaninecarboxamide compounds, respectively, with a tertiary amine. If compounds of the formula (1) which, in addition to the cationic groups, also contain free sulfo or carboxyl groups are desired, the phthalocyanine sulfochlorides or phthalocyaninecarboxylic acid chlorides are reacted with less than stoichiometric amounts of amines of the formulae (2) to (5), and, if desired after quaternisation, the remaining free $SO_2Cl$ or $COCl$ groups, respectively, are hydrolysed to give the sulfo or carboxyl groups or salts thereof, respectively.

Compounds of the formula (1) having substituents of the formula $-(CH_2)_q-Y_3^\oplus$ in which $q=1$ can be obtained from the corresponding chloromethylphthalocyanines obtained by chloromethylation, for example, by reacting the latter with a tertiary amine. Compounds of the type mentioned in which $q=0$ can be prepared in a similar manner from chlorinated phthalocyanines.

Alternatively, the abovementioned compounds can be obtained by using a correspondingly substituted phthalicanhydride or phthalodinitrile (or the corresponding derivatives of naphthalenedicarboxylic acids) as the starting material and subjecting these in a known manner to a condensation reaction leading to the phthalocyanine or naphthalocyanine ring system. If a substituted phthalodinitrile (and the corresponding naphthalene derivative) is used, this compound is fused, if appropriate together with a metal salt, or is cyclised to give the phthalocyanine or naphthalocyanine ring system in solution or in suspension. If the corresponding phthalicanhydride (and the corresponding naphthalene derivative) is used, urea and, if desired, a catalyst, for example boric acid or ammonium molybdate, are also added before the reaction.

In the methods last mentioned, the quaternary ammonium or ternary sulfonium groups can already be present in the phthalic acid starting derivatives, or the corresponding tertiary amines or the corresponding mercaptans can be quaternised or ternised subsequently in the synthesised phthalocyanine ring system.

If the substitution reactions described above are not carried out directly with the metal complexes, or if the reactions to synthesise the phthalocyanine ring system are not carried out in the presence of a compound of the central atom Me, a correspondingly substituted, metal-free phthalocyanine can subsequently be reacted in a solvent with a salt of the central atom Me or an alcoholate thereof. Examples of suitable solvents are mixtures of water and organic solvents, especially also tertiary amines or anhydrous organic solvents, for example pyridine or chlorobenzenes.

The reactions outlined above for the preparation of phthalocyanines containing cationic groups are described in greater detail in EP A-3,149 and 35,470. The compounds, according to the invention, having cationic groups can be prepared analogously to the processes described therein.

The synthesis of the phthalocyanine ring skeleton from derivatives of phthalic acid, with the formation of chlorinated phthalocyanines, is described in Ullmann's Encyclopädie der technischen Chemie ("Ullmann's Encyclopaedia of Industrial Chemistry"), 4th edition, volume 18, page 507 et seq. and in F. H. Moser, A. L. Thomas, "Phthalocyanines" (1963), page 104 et seq. The processes described therein also apply to the synthesis of the naphthalocyanine ring skeleton. As already mentioned earlier, some substituents imparting solubility in water can already be present in the starting compounds, or they can be introduced subsequently into the ring system which has been synthesised as described and is still unsubstituted or already contains substituents Y. It will readily be understood that the methods mentioned above can be combined in any desired manner, so that compounds of the formula (1) containing different substituents A and/or Y in the molecule are formed.

The unsubstituted Si(IV)-, P(V)-, Ti(IV)-, Ge(IV)-, Cr(VI)-, Ga(III)-, Zr(IV)-, In(III)-, Sn(IV)- and Hf(IV)-phthalocyanines (pigments) are also known from the literature. Reference should also be made to the experimental section below for their preparation.

The compounds, according to the invention, of the formula (1) have excellent photosensitising properties and are outstanding producers of singlet oxygen. They can, therefore, be used in accordance with the invention as photosensitisers, photoactivators (these two terms are frequently used synonymously in the literature) and/or singlet oxygen producers. The fields in which they can be used are very multifarious. The compounds of the formula (1) can be employed in all cases where photocatalysed reactions are intended to take place, in particular with the aid of singlet oxygen. These can, for example, be photocatalysed reactions in organic chemistry and also in polymer chemistry. Surprisingly, in some respects the compounds according to the invention have better or more advantageous properties than known photoactivators.

However, the compounds according to the invention are preferably used as photodynamically active agents (i.e. agents which, under the action of light, are effective especially against microorganisms) and, in particular, as photobleaching agents. They are therefore used, for example, for bleaching or removing spots from textiles and for controlling microorganisms in or on organic or inorganic substrates or for protecting the latter against attack by microorganisms, especially as bleaching agents or antimicrobial active substances in detergents and washing liquors, but also as disinfectants for laundry goods, solid surfaces, swimming pools and effluent from sewage treatment plants.

The present invention also relates to a process for carrying out a photosensitised (photoactivated) reaction or a reaction catalysed by singlet oxygen, wherein one or more phthalocyanine compounds of the formula (1), in the presence of oxygen, are brought into contact with the medium in which or on which the said reaction is to take place, or are incorporated in this medium, and are irradiated with light.

In particular, the present invention relates to a process for bleaching or removing spots from textiles and for controlling microorganisms in or on organic or inorganic substrates or for protecting the latter against attack by microorganisms, wherein the textiles or the substrates to be freed from or protected against microorganisms, are treated with phthalocyanines defined in formula (1), in the presence of water and while being irradiated with light.

In order to develop their antimicrobial activity, the phthalocyanine compounds according to the invention require the presence of oxygen and water as well as irradiation with light. Treatment is therefore generally carried out in aqueous solutions or on moist substrates, and the source of oxygen used is the oxygen dissolved in the water or atmospheric oxygen.

The irradiation can be effected by means of an artificial source of light or by means of sunlight. A good effect is achieved, for example, by means of light within the range between about 300 and 2500 nm. Thus irradiation can be carried out, for example, using a commercially available incandescent lamp. The intensity of illumination can vary within wide limits. It depends on the concentration of active substance, on the nature of the substrate or on the substances additionally present which influence the light yield. A further parameter which can be varied is the exposure time, i.e. for the same effect exposure must be longer at a lower light intensity than at a higher intensity. In general, depending on the field of use, exposure times of a few minutes up to a few hours are possible.

If the process is carried out in an aqueous liquor (for example the sterilisation of textiles), the irradiation with light can either be carried out directly in the treatment liquor by means of an artifical source of light mounted inside or outside the liquor, or the substrates, in a moist state, can subsequently either be irradiated, again by means of an artificial source of light, or can be exposed to sunlight.

Good antimicrobial effects can be achieved even with very low concentrations of active substance, for example at 0.001 ppm. Depending on the field of use and on the phthalocyanine derivative employed, a concentration between 0.005 and 100, preferably 0.01 and 50, ppm is preferable. Since the active substances are dyes, the upper limit of concentration is given by the fact that an undesirable colouration of the substrates would be observable if it were exceeded. The upper limit of concentration is thus limited by the strength of the intrinsic colour of the agents employed, but it can be 1000 ppm or more.

The phthalocyanine compounds of the formula (1) employed in the process according to the invention have an extremely broad spectrum of activity against microorganisms. Thus it is possible to control, in particular, Gram-positive bacteria, but also Gram-negative bacteria or to protect various substrates against attack by these bacteria by means of the process according to the invention. An action against fungi and yeasts is also observed.

Substances which increase the action can also be added in the process according to the invention, inter alia electrolytes, for example inorganic salts, for instance sodium chloride, potassium chloride, sodium sulfate, potassium sulfate, sodium acetate, ammonium acetate, alkali metal phosphates and alkali metal tripolyphosphates, especially sodium chloride and sodium sulfate. These salts can be added to the agents according to the invention or can be added directly in the application process, so that they are present in the application solution in a concentration of, preferably, 0.1 to 10%.

By virtue of the broad spectrum of action mentioned against microorganisms, the process according to the invention or the agents according to the invention can be employed in a number of fields of use, examples of which are listed below.

The sterilisation of textiles of synthetic or natural origin may be mentioned as an important application. Thus, material to be washed in the household or in industry can be disinfected by means of the process according to the invention. The material to be washed can be treated for this purpose in the manner mentioned above with aqueous solutions of the phthalocyanine derivatives according to the invention, while being irradiated with light. The phthalocyanine dye can advantageously be present in the treatment liquor in a concentration of 0.01 to 50 mg/l. The sterilisation can also be carried out advantageously together with the washing process. For this purpose, the material to be washed is treated with a wash liquor containing customary detergent substances, one or more phthalocyanine derivatives according to the invention and, if desired, inorganic salts and/or further substances having an antimicrobial action. The washing process can be carried out manually, for example in a tub, or can be carried out in a washing machine. The necessary exposure to light can be effected during the washing process by means of suitable light sources, or the moist material being washed can also, subsequently, for example during drying, either be exposed to a suitable artifical source of light or simply exposed to sunlight.

The compounds of the formula (1) can be added directly to the disinfection liquor or bleach or wash liquor. They can also be incorporated into soaps or detergents containing known mixtures of detergent substances, for example soap in the form of flakes and powder, synthetics, soluble salts of sulfonic acid half-esters of higher fatty alcohols, arylsulfonic acids containing higher and/or multiple alkyl substituents, sulfocarboxylic acid esters of medium to higher alcohols, fatty acid acylaminoalkylglycerolsulfonates or acylaminoarylglycerolsulfonates, phosphoric acid esters of fatty alcohols and the like, builders, for example alkali metal polyphosphate and polymetaphosphate, alkali metal pyrophosphates, phosphate substitutes and additives, such as alkali metal salts of carboxymethylcellulose and other soilredeposition inhibitors, and also alkali metal silicates, nitrilotriacetic acid, ethylenediaminotetraacetic acid, foam stabilisers, such as alkanolamides of higher fatty acids, and, if desired, antistatic agents, fat-restoring skin protection agents, such as lanolin, enzymes, perfumes and dyes, fluorescent brighteners, further inorganic salts and/or further anti-microbial active substances or bleaching agents.

The process according to the invention can also be used to impart an antimicrobial finish to textiles, since the phthalocyanine derivatives according to the invention are readily absorbed by the fibres and ensure a long-lasting effect.

A further field of use for the process according to the invention and for the agents according to the invention is the disinfection of hospital linen, medical articles for daily use and pieces of equipment and floors, walls and furniture (surface disinfection) both generally and particularly in hospitals. The disinfection of hospital linen can be carried out in the manner described above for general material to be washed. The other articles, and also the surfaces of floors and walls, can be treated with aqueous solutions containing the phthalocyanine compounds according to the invention, and, in the course thereof or subsequently, can be exposed to suitable sources of light. The disinfection solutions can, in addition, also contain detergent substances, other compounds having a microbial action and/or inorganic salts.

Surface disinfection can be achieved, for example, by applying (for example by spraying) to the appropriate surface, an aqueous solution of the phthalocyanine compounds according to the invention, this solution preferably containing about 0.001–50 ppm of active substance. The solution can also contain, in addition, other customary additives, for example wetting agents, dispersing agents or emulsifiers, detergent substances and, if desired, inorganic salts. After the solution has been applied, the surface is simply exposed to sunlight or, if required, it can in addition be irradiated by means of an artificial source of light, for example an incandescent lamp. It is advisable to keep the surface moist during the exposure to light.

The process according to the invention and/or the agents according to the invention can also be employed with advantage for sterilising or disinfecting swimming baths. For this purpose it is advantageous to add one or more of the compounds of the formula (1), preferably in an amount of 0.001 to 50, in particular 0.01 to 10, ppm to the water in the swimming bath. Exposure is effected merely by means of sunlight. If desired, additional exposure by means of builtin lamps can be provided. It is possible, by means of the process described, to keep the water of swimming pools free from undesirable germs and to maintain the quality of the water in an excellent state.

The process according to the invention can also be used for sterilising effluents from sewage treatment plants. This is effected by adding to the effluent, for example, 0.001–100, in particular 0.01–10, ppm of one or more of the compounds of the formula (1). Irradiation is advantageously effected by means of sunlight; if desired, additional irradiation can be carried out by means of artifical sources of light.

Possible uses mentioned above represent only one exemplary enumeration of the very wide applicability of the process according to the invention and thus of the phthalocyanines, according to the invention, of the formula (1).

The process according to the invention is particularly preferred for bleaching and removing spots from textiles.

The bleaching and spot-removal process according to the invention, in which the phthalocyanine compounds according to the invention are used, i.e. the treatment of textiles with these compounds, is preferably carried out in an aqueous liquor and especially in a neutral or alkaline pH range.

The phthalocyanines according to the invention are advantageously employed in amounts of 0.01 to 100, in particular 0.01 to 50, mg/l of treatment liquor, it being possible for the amount employed to vary depending on the number of groups imparting solubility in water and on the nature of the substituent $R_2$.

The process is preferably carried out as a combined washing and bleaching process, in which case the aqueous liquor also contains an organic washing agent, such as soap or synthetic washing agents (detergent substances) and, if desired, also other washing agent additives, such as soil-suspending agents, for example sodium carboxymethylcellulose, complex-formers, such as sodium tripolyphosphate, sodium silicate and sodium ethylenediaminetetraacetate and fluorescent brightening agents. Examples of suitable detergent substances are those which have been enumerated earlier in the text in connection with the use of the compounds of the formula (1) in disinfection liquors or bleach or wash liquors and in connection with the relevant washing agents. The phthalocyanine according to the invention can, therefore, either be already incorporated in the appropriate washing agent or can be added subsequently to the wash liquor. The process can, however, also be carried out as a bleaching process alone, without the addition of washing agents. In this case it is advantageous for the treatment liquor to contain an electrolyte, for example sodium chloride, sodium sulfate or sodium tripolyphosphate, in order to ensure the absorption of the phthalocyanine dye. The amounts of electrolyte can be about 0.5 to 20 g/l.

As mentioned above, the wash or bleach liquors can, if desired, also contain one or more fluorescent brighteners. These can be customary fluorescent brighteners for washing agents. It is preferable, however, to employ fluorescent brighteners belonging to the classes comprising distyrylbiphenylsulfonic acids and salts thereof and/or 4,4'-bis-(1,2,3-triazol-2-yl)-stilbenedisulfonic acids and salts thereof. Very particularly good bleaching effects which are higher than would be expected from the additive action of the individual components are achieved by means of these fluorescent brighteners in combination with the photoactivators according to the invention. Suitable fluorescent brighteners of this type are, in particular, those of the formula (A1) indicated later in the text, for example those of the formula (A2) and very particularly preferentially those of the formula (A3). Fluorescent brighteners of the formula (A4) also produce good results, as do mixtures of the fluorescent brighteners of the formulae (A3) and (A4).

The bleaching process according to the invention is advantageously carried out at temperatures within the range from about 20 to 100, in particular 20° to 85° C., for a period of time amounting to 15 minutes to 5 hours, preferably 15 minutes to 60 minutes.

The presence of oxygen and irradiation with light is necessary for the bleaching process according to the invention. The oxygen dissolved in the water or present in the atmosphere is sufficient as a source of oxygen.

Irradiation can be effected by means of an artificial source of light (for example an incandescent lamp or infrared lamp), and it is possible to irradiate the bleach or wash liquor directly, either by means of a light source within the container in which the liquor is present (for example a lamp in the washing machine), or by means of a light source outside the container. Equally, however, it is also possible to carry out the irradiation only after the textiles have been removed from the treatment liquor. In this case, however, the textiles should still be moist or they must be re-moistened subsequently. Sunlight can, however, be used with particular advantage as the source of light, the textiles being exposed to sunlight either during a treatment in the steeping liquor or, in a moist state, after the treatment in the wash or bleach liquor. The source of light used should preferably supply light within a wavelength range of 300–800 nm.

Although the compounds of the formula (1) generally produce very good bleaching effects, the compounds of the formula (1) which are substituted by anionic groups (A=anionic groups, in particular those in which A=-$SO_3^{\ominus}$, $COO^{\ominus}$, $SO_2^{\ominus}$, $SO_2N^{\ominus}CN$ and $SO_2N^{\ominus}$—$SO_2$—$R_6$ and especially those in which A=$SO_3^{\ominus}$, are preferred for use in customary washing, bleaching and steeping agents which usually contain anionic and/or nonionic detergent substances. Of course, compounds of the formula 1 which contain nonionic groups A may also be present in such washing agents.

If they are used as photobleaching agents for textiles, compounds, according to the invention, of the formula (1) which contain cationic groups imparting solubility in water are preferably employed in conjunction with cationic textile treatment agents, for example with cationic surfactants, softeners, antistatic agents, fluorescent brighteners and/or antimicrobial agents. These cationic textile treatment agents can, for example, be added to the washing, bleaching, rinsing, steeping or after-treatment liquor separately from the cationic photobleaching agent. They can, however, also be already incorporated, together with the latter, in a textile treatment agent, in particular a washing, bleaching, steeping or rinsing agent. The individual cationic ingredients which can preferably be employed in conjunction with a cationic photobleaching agent of the formula (1) are described later in the text in relation to the corresponding agents. The process, according to the invention, for bleaching by means of compounds of the formula (1) can also be carried out in the presence of reducing agents. This "reductive" bleaching can in some cases (depending on the substrate, type of dirt and the like) produce an improvement in the bleaching effect. It is preferable to use a reducing agent which has a reduction potential $E_0 < 3.0$ eV, in particular $<0.8$ eV. These reducing agents can be added direct to the bleach (wash) liquor or they can be already present in appropriate washing, steeping, rinsing or bleaching agents together with the photobleaching agent and the customary detergent substances and other washing agent ingredients. The addition of the reducing agents mentioned is particularly advantageous if the photobleaching is carried out in the steeping process. Preferred reducing agents which are suitable in the bleaching process according to the invention are described below at the description of the agents containing the photoactivators according to the invention. The present invention also relates to photosensitising (photoactivating) agents and/or agents producing singlet oxygen which contain one or more of the phthalocyanine compounds defined in formula (1).

The present invention also relates, therefore, to agents for carrying out the process according to the invention, in particular agents having an antimicrobial action, and to bleaching, washing, rinsing and steeping agents. These agents contain one or more phthalocyanine compounds, according to the invention, of the formula (1). In addition, depending on the mode of use, the said agents can also contain customary formulation ingredients.

Preferred agents of this type contain one or more phthalocyanine compounds according to the invention, one or more inorganic salts, for example NaCl, KCl, NaBr, KBr, $K_2SO_4$, $Na_2SO_4$, $K_2CO_3$, $Na_2CO_3$, $NaHCO_3$ and others, in particular NaCl and/or $Na_2SO_4$, and, if desired, water. For example, an agent of this type consists of about 1–80% of a compound of the formula (1), 1–40% of NaCl and/or $Na_2SO_4$ and 0–95% of water. These agents can thus be in a solid form (for example granules) or as an aqueous solution, for example in the form of a 5–50%, for example 5–20%, solution.

In addition to the phthalocyanine active substance, washing, steeping and rinsing agents according to the invention and having a bleaching action contain, for example, customary ingredients of washing agents, for example one or more organic detergents, if desired alkaline builder salts and, if desired, further bleaching agents, for example per compounds, for instance a perborate, percarbonate and the like.

The washing agents or steeping agents according to the invention contain, for example, the known mixtures of detergent substances, for example soap in the form of flakes and powders, synthetics, soluble salts or sulfonic acid halfesters of higher fatty alcohols, arylsulfonic acids containing higher and/or multiple alkyl substituents, sulfocarboxylic acid esters of medium to higher alcohols, fatty acid acylaminoalkylglycerolsulfonates or acylaminoarylglycerolsulfonates, phosphoric acid esters of fatty alcohols and the like. Examples of suitable additives, complex-formers, bleaching agents and the like are alkali metal salts of carboxymethylcellulose and other soil-redeposition inhibitors, and also alkali metal silicates, alkali metal carbonates, alkali metal borates, alkali metal perborates, alkali metal percarbonates, nitrilotriacetic acid, ethylenediaminotetraacetic acid and foam stabilisers, such as alkanolamides of higher fatty acids. The following, for example, can also be present in the washing agents: antistatic agents, fat-restoring skin protection agents, such as lanolin, enzymes, antimicrobial agents, perfumes and fluorescent brighteners.

The washing agents or steeping agents according to the invention preferably contain the phthalocyanine compounds of the formula (1) in an amount of 0.0005 to 1.5, in particular 0.005–1, % by weight, based on the total washing or steeping agent.

Washing or steeping agents according to the invention and having a bleaching action contain, for example, 0.005–1% by weight of the said phthalocyanine compounds, 10–50% by weight of an anionic, nonionic, semipolar, ampholytic and/or Zwitter-ionic surface-active substance, 0–80% of an alkaline builder salt and, if desired, further customary ingredients of washing agents, for example those mentioned above.

Examples of surface-active substances in the said agents are also water-soluble alkylbenzenesulfonates, alkylsulfates, ethoxylated alkyl ether-sulfates, paraffinsulfonates, α-olefinsulfonates, α-sulfocarboxylic acids, salts and esters thereof, alkyl glyceryl ether-sulfonates, fatty acid monoglyceridesulfates or monoglyceridesulfonates, alkylphenol polyethoxy-ether-sulfates, 2-acyloxyalkanesulfonates, β-alkyloxyalkanesulfonates, soaps, ethoxylated fatty alcohols, alkylphenols, polypropoxyglycols, polypropoxyethylenediamines, amine oxides, phosphine oxides, sulfoxides, aliphatic secondary and tertiary amines, aliphatic quaternary ammonium, phosphonium and sulfonium compounds or mixtures of the said substances.

Examples of alkaline builder salts, which can be present in the agents according to the invention, for instance, in an amount of 10–60% by weight are, inter alia: water-soluble alkali metal carbonates, borates, phosphates, polyphosphates, bicarbonates and silicates, water-soluble aminopolycarboxylates, phytates, polyphosphonates and polycarboxylates and water-insoluble aluminium silicates.

As already mentioned, the washing agents or bleaching agents according to the invention can also contain fluorescent brighteners. Suitable brighteners of this type are any of the fluorescent brighteners customary in the washing agent industry. On the other hand, fluorescent brighteners belonging to the classes comprising distyrylbiphenylsulfonic acids and their salts and/or 4,4'-bis-(1,2,3-triazol-2-yl)-2,2'-stilbenedisulfonic acids and their salts and mixtures thereof are employed particularly preferentially in washing or bleaching agents according to the invention. If agents according to the invention contain such fluorescent brighteners, the latter are preferably present in the agents in an amount of 0.005–1.5% in particular 0.01–0.5%, based on the total weight of the agent. Fluorescent brighteners which can be employed are, in particular, those of the formula

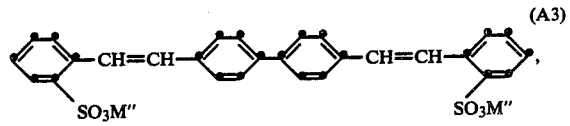

in which M" is hydrogen, sodium or potassium, and/or of the formula

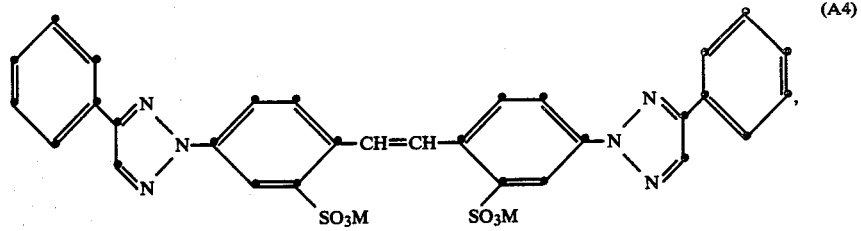

in which M is hydrogen or an alkali metal ion, ammonium ion or amine salt ion.

The washing agents, according to the invention, having an antimicrobial activity preferably contain the phthalocyanine compounds according to the invention in an amount of 0.0005 to 1.5, in particular 0.005 to 1, % by weight, based on the total washing agent.

In other respects washing agents, according to the invention, having an antimicrobial action can have the same composition as described earlier in the text for the washing and steeping agents, according to the invention, having a bleaching action.

In the washing/bleaching and steeping agents described above which contain, as detergent substances, especially anionic, nonionic, semipolar, ampholytic and/or Zwitterionic surface-active substances, it is preferable to use phthalocyanine compounds of the formula

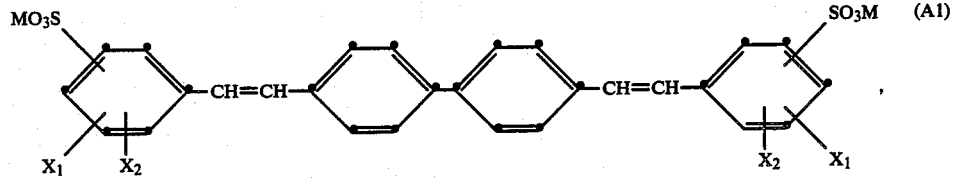

in which $X_1$ is hydrogen, chlorine, bromine or alkyl or alkoxy each of which has 1 to 4 C atoms, $X_2$ is hydrogen or alkyl having 1 to 4 C atoms and M is hydrogen or an alkali metal ion, ammonium ion or amine salt ion, especially those of the formula

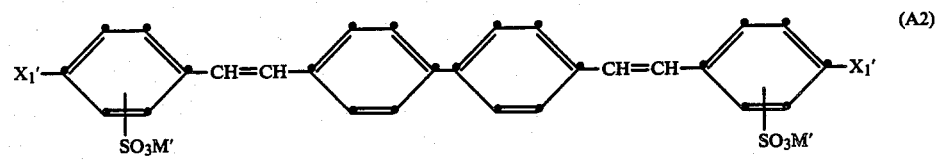

in which $X_1'$ is hydrogen or chlorine and M' is hydrogen, sodium, potassium or ammonium, and preferably of the formula (1) which contain anionic or nonionic, preferably anionic, groups imparting solubility in water, although the corresponding cationic compounds produce good bleaching effects. Compounds of the formula (1) which are particularly preferred in this respect are those in which A is $SO_3^\ominus$, $COO^\ominus$, $SO_2^\ominus$, $SO_2N^\ominus CN$ and/or $SO_2N^\ominus$—$SO_2$—$R_6$, in particular $SO_3^\ominus$.

The phthalocyanine compounds of the formula (1) which are substituted by cationic groups A are preferably employed as photobleaching agents for textiles in washing, steeping, rinsing or after-treatment agents containing cationic textile treatment agents, for example cationic surfactants, softeners, antistatic agents, fluorescent brighteners and/or antimicrobial agents. In agents of this type the action of the cationic phthalocyanines of the formula (1) become particularly effective.

Examples of cationic textile treatment agents (for example surfactants, softeners, antistatic agents or fluorescent brighteners) which can be present in the agents according to the invention are indicated in EP A-35,470 from page 10, paragraph 2 to page 16, paragraph 2. These descriptive sections are hereby declared to form a part of the present application. Compositions of cationic textile treatment agents of this type are also described in the Examples of the said EP A. The cationic phthalocyanines, according to the invention, of the formula (1) can be incorporated analogously in agents of this type. Such agents, especially textile after-treatment agents and rinsing agents, are as a rule liquid. The active substances present therein are preferably emulsified in water. The textile treatment agents (rinsing, after-treatment and washing agents) according to the invention can, in addition, also contain other optional ingredients as well as the active substances mentioned. Examples of such ingredients are also described in EP A-35,470 from page 16, last paragraph, to page 22, first paragraph. This description is hereby also regarded as forming part of the present application.

Preferred cationic textile treatment agents, i.e. especially softeners, antistatic agents or surfactants, in the agents described above which contain cationic compounds of the formula (1), are as follows:

(1) Quaternary ammonium salts of the formula

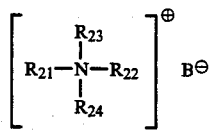

in which $R_{21}$ is hydrogen or an aliphatic group having 1 to 22 C atoms, $R_{22}$ is an aliphatic group having 10 to 22 C atoms, $R_{23}$ and $R_{24}$ independently of one another are alkyl having 1 to 4 C atoms and $B^{\ominus}$ is an anion.

The following are examples of quaternary ammonium softeners: tallyltrimethylammonium chloride, ditallyldimethylammonium chloride, ditallyldimethylammonium sulfate, dihexadecyldimethylammonium chloride, dioctadecyldimethylammonium chloride, dieicosyldimethylammonium chloride, didocosyldimethylammonium chloride, dihexadecyldiethylammonium chloride, dihexadecyldimethylammonium acetate, ditallyldipropylammonium phosphate, ditallyldimethylammonium nitrate and dicocoyldimethylammonium chloride.

(2) Quaternary imidazolinium salts of the formula

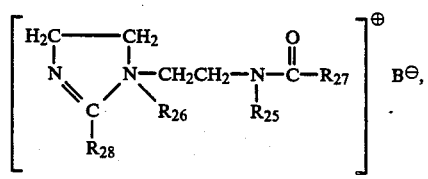

in which $R_{25}$ is hydrogen or alkyl having 1 to 4 C atoms. $R_{26}$ is alkyl having 1 to 4 C atoms, $R_{27}$ is alkyl having 1 to 22 C atoms, $R_{28}$ is hydrogen, or alkyl having 1 to 22, preferably 15–22, C atoms and $B^{\ominus}$ is an anion. $R_{27}$ and, if appropriate, also $R_{28}$ are each alkyl having 12 to 22 C atoms.

The following are examples of preferred imidazolinium compounds of the above formula: 1-methyl-1-stearoylamidoethyl-2-heptadecyl-4,5-dihydroimidazolinium methosulfate, 1-methyl-1-palmitoylamidoethyl-2-octadecyl-4,5-dihydroimidazolinium chloride and 2-tallyl-1-methyl-1-talloylamidoethyl-4,5-dihydroimidazolinium methosulfate.

All the washing, rinsing, steeping and after-treatment agents, according to the invention and having a bleaching action, described above, which contain one or more phthalocyanines of the formula (1) as photobleaching agents, can, if desired, additionally contain a reducing agent. Depending on the dirt and substrate to be treated, the presence of such an agent improves the bleaching action of the photoactivator in some cases. Application is effected in a customary manner (irradiation with light). Particularly good results are achieved using this "reductive bleaching" in the steeping process. For this purpose, the textiles are steeped in a liquor containing the steeping (washing) agent together with the photoactivator and the reducing agent, and are irradiated directly with light, preferably with sunlight.

Suitable reducing agents are substances such as are defined and described as electron donors in EP A-87,833. In particular, reducing agents having a reduction potential of <3.0 eV, especially <0.8 eV, can be used. Examples of reducing agents of this type (electron donors) are alkali metal sulfites, cysteine, alkali metal thiosulfates, Fe(II) salts, such as FeSO$_4$, Sn(II) salts, such as SnCl$_2$, and the like. Of these, alkali metal sulfites, in particular sodium sulfite, are preferred. If a reducing agent (electron donor) mentioned above is present in washing, bleaching, steeping or rinsing agents according to the invention, its concentration is, for example, 1 to 40% by weight, based on the total agent.

The examples below illustrate in greater detail the processes for the preparation of the phthalocyanine compounds according to the invention, the use of the latter and agents containing them, without thereby expressing a limitation on the subject matter of these examples. In the examples, just as in the remainder of the description, parts and percentages are always by weight, unless stated otherwise.

EXAMPLE 1

30 parts of zirconium(IV) phthalocyanine are introduced slowly into 140 parts by volume of chlorosulfonic acid at room temperature. After stirring for one hour, the reaction temperature is raised to 70° to 75° C. and is kept there for 2 hours. The temperature is then kept at 100° to 105° C. for 3 hours and then at 120° to 125° C. for 4 hours, with continuous stirring. When the reaction mass has cooled, it is discharged into ice water, in the course of which the temperature does not exceed 0° C. The resulting suspension is filtered with suction, and the residue is washed with 1000 parts of ice water. The material on the filter is stirred in 500 parts of water, the pH is adjusted to 10 with sodium hydroxide solution, and the mixture is heated at 80° C. until complete solution takes place. The solution is evaporated to dryness in vacuo. 22.5 parts of a powder which gives a blue solution in water are obtained. Analysis shows that the phthalocyanine molecule has been substituted by 3 sulfonic acid groups on average. The product obtained thus has the approximate formula $$Zr(IV)Pc(SO_3Na)_{ca.3}, \quad (101)$$

in which Zr(IV)Pc is the radical of the Zr(IV) phthalocyanine and it has a $\lambda_{max}$ of 683 nm (measured in 1:1 dimethylformamide/water).

The zirconium(IV) phthalocyanine required as starting material is known. See, for example, Žurnal Nauk. Khem. (Russian Journal of Inorganic Chemistry) 9, 125 (1964).

EXAMPLE 2

20 parts of titanium(IV) phthalocyanine are introduced slowly into 90 parts by volume of chlorosulfonic acid at room temperature. After being stirred for one hour, the reaction mixture is heated to 110° C. and is kept at this temperature for 2 hours. The mixture is then cooled immediately and the mass is discharged into ice water. The resulting suspension is filtered with suction, and the residue is washed with ice water. The material on the filter is stirred in 500 parts of water, and 5 parts by volume of pyridine are added. The pH value is kept at a value of 7 to 8 until it no longer falls, by adding sodium hydroxide solution at a temperature of 20° to 25° C. The resulting solution is evaporated to dryness in vacuo. 17.5 parts of a powder soluble in water to give a blue colour are obtained. Analysis shows that the phthalocyanine molecule has been substituted by 3 sulfonic acid groups on average. The product obtained thus has the approximate formula $$\text{Ti(IV)Pc(SO}_3\text{Na)}_{ca.3} \qquad (102),$$

in which Ti(IV)Pc is the radical of Ti(IV) phthalocyanine, and it has a $\lambda_{max}$ of 692 nm (measured in 1:1 dimethylformamide/water).

The titanium(IV) phthalocyanine required as starting material is known from literature. See, for example, Žurnal Nauk. Khem. (Russian Journal of Inorganic Chemistry) 9, 478 (1964).

EXAMPLE 3

30 parts of germanium(IV) phthalocyanine are introduced slowly into 140 parts by volume of chlorosulfonic acid at room temperature. After being stirred for one hour, the reaction mixture is heated to 100° to 105° C. After 2 hours the reaction temperature is raised to 115° to 120° C. and is kept at this temperature for a further 2 hours. After cooling to room temperature, the reaction mass is discharged into ice water, the resulting suspension is filtered with suction and the residue is washed with ice-cold 5% sodium chloride solution. The material on the filter is stirred in 1000 parts of water, and 10 parts by volume of pyridine are added. The pH is kept at a value of 9 to 9.5 until it no longer falls, by adding sodium hydroxide solution at a temperature of 20° to 25° C. The solution is evaporated to dryness in vacuo. 58 parts of a powder soluble in water to give a blue colour are obtained.

Analysis shows that the phthalocyanine molecule has been substituted by 2.8 sulfonic acid groups on average. The product therefore has the approximate formula $$\text{Ge(IV)Pc(SO}_3\text{Na)}_{ca.2.8} \qquad (103)$$

in which Ge(IV)Pc is the radical of Ge(IV) phthalocyanine and it has a $\lambda_{max}$ of 680 nm (measured in 1:1 dimethylformamide/water).

The germanium(IV) phthalocyanine required as starting material is known from the literature. See, for example, J. Amer. Chem. Soc. 82, 5790 (1960).

EXAMPLE 3a 30 parts of germanium(IV) phthalocyanine are introduced slowly into 140 parts by volume of chlorosulfonic acid at room temperature. After being stirred for one hour, the reaction mixture is heated to 100° to 105° C. After 2 hours the reaction temperature is raised to 115° to 120° C. and is kept at this temperature for a further 2 hours. After cooling to room temperature, the reaction mass is discharged into ice water, the resulting suspension is filtered with suction and the residue is washed with ice-cold 5% sodium chloride solution.

The sulfochloride paste thus obtained is suspended in 600 parts of ice water, 11 parts of cyanamide are added and the pH is kept at 10 by means of sodium hydroxide solution. The reaction mixture is stirred at room temperature until the pH remains constant without the addition of further sodium hydroxide solution. The resulting solution is evaporated to dryness. 70 parts of a blue powder are obtained.

35 parts of the powder obtained are dissolved in 500 parts of water, the pH is adjusted to 2 with concentrated hydrochloric acid, and the solution is evaporated to dryness. The residue is finely pulverised and then stirred in 250 parts by volume of 1N hydrochloric acid.

The suspension is filtered, and the residue is washed with 250 parts by volume of 1N hydrochloric acid. The material on the filter is mixed with 400 parts of water, the pH of the solution is adjusted to 7 by means of sodium hydroxide solution and it is then evaporated. 21 parts of a blue powder are obtained.

The compound thus obtained has the formula $$\text{Ge(IV)Pc} \overset{\ominus}{+} \text{SO}_2-\text{N}-\text{CN Na}^{\oplus}]_{ca.\,2.8}$$
$$(\lambda_{max} = 680 \text{ nm}).$$

EXAMPLE 4

5 parts of Pc(SO$_3$Na)$_{ca.3}$ (sodium phthalocyaninetrisulfonate) are dissolved in 100 parts by volume of 1:1 pyridine/water. 1 part of indium(III) nitrate is added to the solution, and the mixture is then heated at reflux temperature for 12 hours. The reaction mixture is clarified by filtration and then evaporated to dryness in vacuo. 5.6 parts of a water-soluble powder are obtained. The product obtained has the formula $$\text{In(III)Pc(SO}_3\text{Na)}_{ca.} \qquad (104)$$

in which In(III)Pc is the radical of In(III) phthalocyanine, and has a $\lambda_{max}$ of 668 nm (measured in 1:1 dimethylformamide/water).

EXAMPLE 5

The procedure of example 4 is repeated, except that gallium(III) nitrate is employed instead of indium(III) nitrate, affording the product of the formula $$\text{Ga(III)Pc(SO}_3\text{Na)}_{ca.3} \qquad (105)$$

in which Ga(III)Pc is the radical of Ga(III) phthalocyanine, in the form of a water-soluble powder having a $\lambda_{max}$ of 679 nm (measured in 1:1 dimethylformamide/water).

EXAMPLE 6

A cotton fabric weighing 1 g and soiled with tea* is treated at 40° C., while being exposed to a 250 W IR lamp** for one hour, with stirring, in 100 ml of an aqueous wash liquor containing 0.005%, based on the weight of the fabric, of the compound of the formula (103) and 0.5 g of a detergent of the following composition:
Sodium dodecylbenzenesulfonate:16%
Sodium tripolyphosphate:43%
Sodium silicate:4%
Magnesium silicate:2%
Fatty alcohol sulfate:4%
Sodium carboxymethylcellulose:1%
Sodium ethylenediaminetetraacetate:0.5%
Sodium sulfate:29.5%

*The cotton fabric is soiled with tea in the following manner:

15 g of tea ("Fine Ceylon Fannings Tea") are boiled for 1 hour in 600 ml of demineralised water, and the solution is then filtered. The tea leaves filtered off are taken up in 400 ml of demineralised water and boiled again for approx. 60 minutes. The two filtrates are combined and made up to 1000 ml with demineralised water. 45 g of cotton fabric (bleached and mercerised) are treated with this tea for 2½ hours at 100° C. and with continuous agitation; "dyeing" is then carried out in the cooling liquor for a further 16 hours. 5 g of sodium chloride are then added to the tea liquor and treatment is carried out at 100° C. for a further 2½ hours. Finally, the liquor is cooled and the soiled cotton is rinsed twice at 60° C. and dried at 100° C. Finally, the soiled fabric is also washed for 20 minutes at 90° C. and at a liquor ratio of 1:20 with a liquor containing 5 g/l of detergent (see above for composition), subjected to a hot and cold rinse and dried at 100° C. in a circulating air oven.

**Lamp used: "Phillips" infrared lamp (white) 220/230 V, 250 W, using a type 13,372 E/06 reflector. The lamp is mounted approx. 25 cm above the wash liquor.

The piece of fabric is then rinsed and dried and subsequently assessed visually, in the course of which it is found that its brightness is far higher than that of the soiled fabric.

The degree of bleaching of the treated piece of fabric is also determined by measuring the whiteness (brightness value) Y (expressed as a %, based on absolute white as specified in the CIE Recommendation of 1.1.1969) by means of an ®Elrepho spectrophotometer made by ZEISS. The values determined confirm the visual impression and show that, as a result of adding the photosensitiser of the formula (103), a considerable gain in brightness ($\Delta Y$) is achieved, compared with the comparison fabric washed without a photosensitiser.

EXAMPLE 7

The procedure described in Example 6 is repeated, but a fabric soiled with red wine (EMPA test fabric No. 114, see Example 9), bilberry juice or cherry juice is employed instead of the test fabric soiled with tea. These test fabrics are also excellently bleached by means of the photoactivator of the formula (103), and a considerable gain in brightness compared with the comparison fabric washed without photoactivator is also achieved.

EXAMPLE 8

Each of 5 samples of 5 g of a cotton fabric dyed* with a brown dye is put into 500 ml of a wash liquor containing 5 g/l of a detergent of the composition indicated in Example 6 and also 0.005%, based on the weight of fabric, of the compound of the formula (103). The samples to be bleached are washed for 120 minutes at 50° C., with continuous agitation and while exposed to a lamp described in Example 6. The samples are then rinsed and dried, and the degree of bleaching of the dried samples is then measured in the form of brightness values, expressed as a percentage based on the absolute white as specified in CIE Recommendation of 1.1.1969, by means of an ®Elrepho photometer made by ZEISS (standard illuminant D 65, 2 degrees standard observer, measuring diaphragm 35 mm $\phi$). The brightness values measured, which are far higher than those of the dyed fabric before and after washing in the absence of photoactivator, show that the soiled fabric is excellently bleached by means of the photoactivator employed.

* The cotton sample is dyed in the following manner:

150 mg of the commercially available brown dye of the formula

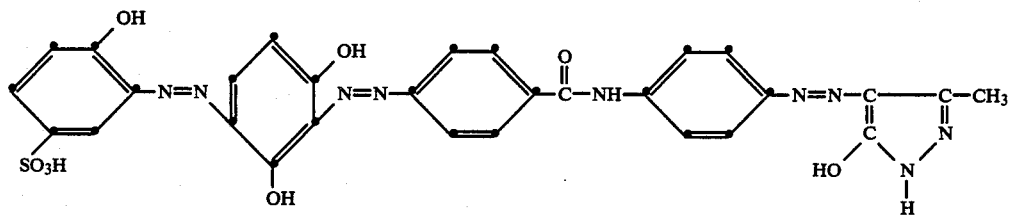

are dissolved, at a temperature of 50° C., in 2000 ml of water containing 1 g of sodium carbonate. 100 g of cotton fabric (bleached and mercerised) are dyed in this dye liquor with continuous agitation by heating the liquor to 90° C. in the course of 30 minutes. Dyeing is carried out at 90° C. for 90 minutes, during which time 20 g of sodium sulfate decahydrate are added in 4 portions of equal size at intervals of 15 minutes. After dyeing, the cotton is subjected to 2 cold rinses and coppered for 20 minutes at 60° C. and at a liquor ratio of 1:20 in a liquor containing 0.75 g/l of crystalline copper sulfate and 1 ml/l of glacial acetic acid. The dyeing is then subjected to 2 cold rinses and dried at 100° C. in a hot air oven.

EXAMPLE 9

10 g portions of a test fabric (EMPA test fabric No. 114, obtainable at the Eidgenössischen Materialprüf- und Versuchsanstalt ("Federal Institution for Testing Materials and Research"), CH-9001 St. Gallen, Unterstrasse 11) which has been soiled with red wine are washed for 30 minutes at 50° C. and at a liquor ratio of 1:50 in wash liquors containing the following ingredients:

Liquor 1: 4 g/l of the detergent of the composition indicated in Example 6,
Liquor 2: 4 g/l of the detergent of the composition indicated in Example 6, 0.0005 g of the compound of the formula (103)
Liquor 3: 4 g/l of the detergent of the composition indicated in Example 6, 1 g/l of sodium perborate and 0.5 g/l of tetraacetylethylenediamine (bleach activator)
Liquor 4: 4 g/l of the detergent of the composition indicated in Example 6, 1 g/l of sodium perborate, 0.5 g/l of tetraacetylethylenediamine and 0.0005 g of the compound of the formula (103).

After being washed, the pieces of fabric are subjected to a brief rinse and are then laid in the sun for 2 hours and moistened several times. The degree of bleaching (the brightness) of the fabric samples is then determined as indicated in Example 6 or 8.

The results obtained show that the fabric samples washed in liquor 2 have appreciably higher brightness values than those washed in liquor 1. The comparison of the washing tests in liquors 3 and 4 shows that the addition of a photoactivator (in this case of the formula (103)) to an activated perborate bleach liquor is capable of causing an additional considerable increase in the brightness of the washed pieces of fabric. The fabric samples washed in liquor 4 are distinctly brighter than those washed in liquor 3.

EXAMPLE 10

A washing agent slurry, consisting of 50 parts of demineralised water and 50 parts of a washing agent of the following composition, is prepared:

8.0% of linear sodium alkylbenzenesulfonate (chain length of the alkyl ester: $C^{-}_{11.5}$), 2.9% of tallow alcohol tetradecanethyleneglycol ether (14 EO), 3.5% of sodium soap (chain length $C_{12-16}$:13–26%; $C_{18}$–$C_{22}$:74–87%), 43.8% of sodium triphosphate, 7.5% of sodium silicate ($SiO_2$:$Na_2O$=3.3:1), 1.9% of magnesium silicate, 1.2% of carboxymethylcellulose, 0.2% of Na ethylenediaminetetraacetate, 21.2% of sodium sulfate, 0.03% of photoactivator of the formula (103), 0.13% of 4,4'-bis-(2-sulfostyryl)-biphenyl, Na salt (fluorescent brightener) and ad 100% of water.

The photoactivator and the brightener are added with substantial exclusion of light to the washing agent slurry defined above, but not yet containing these two components, and the mixture is dried for 4 hours in a drying box under a vacuum of approx. 400 mmHg and at 80° C. The resulting encrustations of washing agent are forced through a sieve under which another sieve is located, so that a washing powder of uniform particle size is produced.

The test substrates used are strips of bleached cotton fabric which have been soiled by fruit juices (cherry, elderberry, blackberry, redcurrant and bilberry juice), tea (see Example 6), blood (EMPA test fabric, type 103, series 23) or red wine (EMPA test fabric No. 114).

Test strips from each of the soiled fabrics just described are washed for 30 minutes at 50° C. and at a liquor ratio of 1:20 in a liquor containing 4 g per litre of the washing agent defined above, and are then subjected to a brief rinse and hung, centrifuge-moist, on a line in the daylight and left to dry for 6 hours, being sprayed every 40 minutes with an alkaline solution of pH 9. These washing tests are also carried out with a washing agent containing no fluorescent brightener or no photoactivator or none of either. The degree of soil removal is assessed visually. A rather modest removal of soil is obtained when the washing agent with no fluorescent brightener or photoactivator is used. Very good and pronounced bleaching effects are achieved in the presence of the photoactivator (without flourescent brightener). When the fluorescent brightener (but no photoactivator) is present, bleaching effects are obtained which are, however, less than when the photoactivator is present. By far the best results in all types of soiling are achieved when photoactivator and fluorescent brightener are present. In each case an extremely bright and strongly bleached cotton fabric results.

The effects obtained on a standardised piece of cotton dyed brown (see Example 8) are evaluated colorimetrically. This fully confirms the results obtained visually.

Entirely analogous results are obtained if 4,440-bis-(4-phenyl-1,2,3-triazol-2-yl)-2,2'-stilbenedisulfonic acid (K salt) is employed as the fluorescent brightener in the washing agent of the composition described above.

EXAMPLE 11

100 parts of a stock washing agent of the composition indicated in Example 6 are made into a slurry with 50 ml of water. 0.02 part of the photoactivator of the formula (103) and 0.15 part of 4,4'-bis-(2-sulfostyryl)-biphenyl, Na salt (fluorescent brightener) are dissolved in a little water, which is added to the washing agent slurry and thoroughly mixed with it. The slurry is dried at 105° C. in a drying cabinet, pulverised and processed as described in Example 10 to give a washing powder of uniform particle size.

A cotton fabric weighing 5 g and dyed with a brown dye in accordance with Example 8 is treated for 30 minutes at 35° C. with 100 ml of a wash liquor containing 0.5 g of the washing powder obtained as described above. Without rinsing, the fabric is then laid on a filter paper impregnated with the wash liquor and irradiated for 90 minutes with a 250 W IR lamp (as described in Example 6; distance of the lamp from the fabric: approx. 30 cm). The fabric is then rinsed and dried, and the degree of bleaching (increase in brightness) is determined as described in Example 6. The whole process (washing, exposure to light and determination of brightness) is repeated five times. Result: up to the 5th cycle, the brightness value of the fabric increases continuously without a tendency to greenish discoloration being discernible.

EXAMPLE 12

Comparable bleaching effects are obtained if a photoactivator of the formula (101), (102), (104) or (105) is employed in Examples 6–11 instead of the photoactivator of the formula (103).

EXAMPLE 13

Test of activity against bacteria

Method

A microbial suspension of Staphylococcus aureus ATCC 6538 having a defined amount of microbes per ml is added to an aqueous solution containing one of the compounds of the formulae (101) to (105) in concentrations of 0.01, 0.1 and 1.0 ppm. This test suspension is in a beaker under a water-cooled sheet of glass in order to prevent heating caused by the subsequent exposure to light. Irradiation is then carried out for 5, 10, 20, 30 and 60 minutes by means of an incandescent lamp or an infrared lamp (Philips IR, 250 W, type 13372 E/06 "Weiss" ("white") infrared lamp), located at a distance of 20 cm above the surface of the suspension. The microbial count is then determined in the customary manner by parallel counting. The reduction in microbes in a particular case is calculated in powers of ten in accordance with the formula $x = -\log_{10} N/N_o$, where $N_o$ is the microbial inoculation and N is the number of microbes surviving.

The results show that the compounds tested reduce the number of test microbes by 2 to 6 powers of ten, depending on the concentration employed and the duration of exposure to light.

EXAMPLE 14

Test of the disinfecting action on textiles

A piece of cotton fabric is clamped on a metal grid and inoculated with a test suspension (containing one of the compounds of the formulae (101) to (105) and a test microbe strain) described in Example 13. The metal grid, which is connected to a motor, is then rotated and irradiated with an infrared lamp. A sheet of glass cooled with running water is placed between the lamp and the piece of fabric, in order to prevent the piece of fabric from being heated. Parallel to this, a piece of fabric is treated under identical test conditions, but with no antimicrobial active substance applied to it. After exposure for 1 hour, the microbial counts are measured quantitatively and the reduction in microbes effected by the particular phthalocyanine is determined. The action against Staphylococcus aureus ATCC 6538 is tested. Reduction in microbes similar to those in Example 13 are found.

EXAMPLE 15

Surface disinfection

Enamelled floor tiles of dimensions $4 \times 4$ cm are inoculated with a microbial suspension of Staphylococcus aureus ATCC 6538; approx. $10^5$ microbes are thereby distributed uniformly over the surface of a floor tile. An aqueous solution containing 1 ppm of one of the compounds of the formulae (101) to (105) is then sprayed on to the surface. The surface is then irradiated for 30 or 45 minutes with an incandescent lamp (250 W, distance: 20 cm). Samples are taken after this time by transfer into Rodac trays. No further microbial growth can be observed after 45 minute treatment with the said compounds.

EXAMPLE 16

Sterilising a sewage treatment plant effluent

A sample of sludge is taken from a laboratory sewage treatment apparatus and is filtered through a paper filter. One of each of the phthalocyanine compounds to be tested, of the formulae (101) to (105) is added to the filtrate, which contains approx. $10^6$ microbes/ml, to give a concentration of 1 ppm of the compound in the filtrate. The latter is then illuminated with standard light, 380–730 nm, at 300 mW/cm$_2$. The number of germs surviving is determined after varying intervals of time. Even after 45 minutes, no more Staphylococci are present. The number of other microbes present in the filtrate also decreases markedly after a longer period of exposure (1 or more hours).

EXAMPLE 17

Sterilising swimming pools

Swimming pools containing 5000 1 of water apiece are installed in the open. The water in each pool is treated with one of the compounds of the formulae (101) to (105), in a concentration of 0.5 ppm. Samples of water are taken at intervals of 1–5 days, and the microbial counts are determined quantitatively. The microbiological testing determines (a) the total microbial count and (b) the number of coliform microbes.

RESULT

In the pool containing none of the phthalocyanine compounds tested, the coliform microbes multiply to $2-3 \times 10^1$ microbes/100 ml. In a pool containing an active substance, no coliform microbes are detected up to the 16th day of the test.

For a further test, a microbial suspension containing Staphylococcus aureus ATCC 6538 and Escherichia coli ATCC 11 229 is added to the water in an amount of 50 microbes per 100 ml of pool content in each case, on the 16th day of the test. A measurement immediately after the introduction of the microbes shows a uniform distribution in the pool. After 24 hours, no coliform microbes nor any Staphylococci are detected in the pool containing the active substance (100 ml of water taken in each case). The total microbial count, consisting of autochtonous microbial flora (native to the swimming pool) remained constant during the period of the test.

What is claimed is:

1. A phthalocyanine compound of the formula

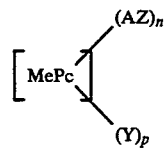

in which MePc is the Ge(IV)-phthalocyanine ring system, A is a group of the formulas $-SO_3^\ominus$, $-SO_2^\ominus$, $-SO_2N^\ominus-CN$, $-SO_2N^\ominus-SO_2-R_6$,

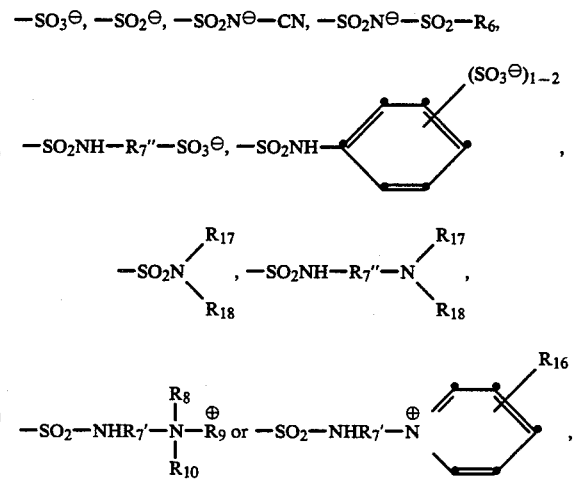

wherein $R_6$ is $C_1$-$C_4$-alkyl, phenyl, ($C_1$-$C_4$-alkyl)-phenyl, chlorophenyl or methoxyphenyl, $R_7'$ is $C_2$-$C_6$-alkylene, $R_7''$ is $C_1$-$C_6$-alkylene, $R_8$, $R_9$ and $R_{10}$ independently of one another are $C_1$-$C_4$-alkyl which is unsubstituted or substituted by hydroxyl, halogen or phenyl, $R_{16}$ is $C_1$-$C_4$-alkyl, halogen or hydroxyl and $R_{17}$ and $R_{18}$ independently of one another are hydrogen, alkyl, hydroxyalkyl or halogenoalkyl being 1–6 C atoms in each case, or phenyl or, together with the nitrogen atom to which they are attached, are the piperidine, piperazine or morpholine ring, Z, as a counter-ion for an anionic group, is a hydrogen ion, alkali metal ion, an unsubstituted ammonium ion or a substituted ammonium ion of the formula

in which R', R" and R'" independently of one another are hydrogen or alkyl of 1–4 carbon atoms which is unsubstituted or substituted by halogen, hydroxyl, phenyl or cyano, at least one R-substituent being other than hydrogen, and two R-radicals together with the ammonium nitrogen can be piperidine, piperazine, morpholine, pyrrolidine or imidazolidine, for a cationic group is a halide ion, alkylsulfate ion, a benzenesulfonate ion, a toluenesulfonate ion, a p-chloro-benzenesulfonate ion, a sulfate ion, a phosphate ion or the ion of an organic carboxylic acid, and, for a nonionic group, is zero, n is number from 1 to 4, p is number from 0 to 4 and Y is halogen, alkyl or phenyl, it being possible for different types of substituents A and/or Y to be present in the molecule.

2. A phthalocyanine compound of claim 1, in which A is a group of the formula $SO_3^{\ominus}$, $-SO_2N^{\ominus}-CN$ or $-SO_2N^{\ominus}-SO_2-R_6$ and Z is a hydrogen, alkali metal or ammonium ion.

3. A phthalocyanine compound according to claim 2, in which A is $SO_3^{\ominus}$.

4. A phthalocyanine compound of claim 2 wherein n is 2 to 4.

5. A phthalocyanine compound of claim 2 wherein p is 0 to 2.

6. A phthalocyanine compound of claim 3 wherein n is 2 to 4.

7. A phthalocyanine compound of claim 3 wherein p is 0 to 2.

* * * * *